United States Patent [19]
Gombotz et al.

[11] Patent Number: 6,036,978
[45] Date of Patent: *Mar. 14, 2000

[54] CONTROLLED RELEASE POLYPEPTIDE COMPOSITIONS AND METHODS OF TREATING INFLAMMATORY BOWEL DISEASE

[75] Inventors: Wayne R. Gombotz, Kirkland; SiowFong Wee, Edmonds, both of Wash.

[73] Assignee: Immunex Corporation, Seattle, Wash.

[*] Notice: This patent issued on a continued prosecution application filed under 37 CFR 1.53(d), and is subject to the twenty year patent term provisions of 35 U.S.C. 154(a)(2).

[21] Appl. No.: 08/636,841

[22] Filed: Apr. 23, 1996

Related U.S. Application Data

[63] Continuation of application No. 08/265,587, Jun. 24, 1994, abandoned.

[51] Int. Cl.⁷ .............................. A61K 9/16; A01N 37/18
[52] U.S. Cl. .................................. 424/491; 514/2
[58] Field of Search ..................... 424/488, 490, 424/491, 499; 514/2

[56] References Cited

U.S. PATENT DOCUMENTS 4,792,452  12/1988  Howard et al. .......................... 424/478
5,302,399   4/1994  Otagiri et al. .......................... 424/493

OTHER PUBLICATIONS

Downs, et al., *J. Cell Phys.*, 152:422 (1992).
Smith, T., *BioPharm*, Apr. 1994, p. 54.
Edelman, et al., *Biomaterials*, 12:619 (1991).
Edelman, et al., *PNAS*, 90:1513 (1993).
Maysinger, et al., *Neuroscience Letters*, 140:71 (1992).
Podolsky, D., *New Eng. J. Med*, Sep. 26, 1991, p. 928 (1991).
Podolsky, D., *New Eng. J. Med*, Oct. 3, 1991, p. 1008 (1991).
Stevens, et al., *Digestive Diseases and Sci.*, 37(6):818 (1992).
Braegger, et al., *The Lancet*, 339:89 (1992).
Garside, et al., *Cytokine*, 5(1):24 (1993).
Wee, et al., *Proc. Intern. Symp. Control. Rel. Bioact. Mater.*, 21 (1994) (abstract).
Smidsrod, et al., *Tibtech*, 8:71 (1990).
Mumper, et al., *J. Control Rel.*, Article 985 (1994).
Segi, et al., *Chem Pharm. Bull.*, 37:3092 (1988).
Stockwell, et al., *J. Control. Rel.*, 3:167 (1986).
Peppel et al., J. Exp. Med. 174:1483–1489, Dec. 1991.

*Primary Examiner*—John Ulm
*Attorney, Agent, or Firm*—Julie K. Smith

[57] ABSTRACT

The invention pertains to a controlled release pharmaceutical formulation that has an effective amount of a polypeptide selected from the group consisting of: (a) TNFR, (b) IL-1R, (c) IL-1ra, (d) IL-6R and (e) a monoclonal antibody that is immunoreactive against TNF, IL-6 or IL-1; wherein the polypeptide is encapsulated in alginate. The invention also pertains to methods of treating inflammatory bowel disease by administering the above composition to a patient in need thereof.

1 Claim, No Drawings

CONTROLLED RELEASE POLYPEPTIDE COMPOSITIONS AND METHODS OF TREATING INFLAMMATORY BOWEL DISEASE

This is a continuation of application Ser. No. 08/265,587, filed Jun. 24, 1994, now abandoned.

FIELD OF THE INVENTION

This invention pertains to controlled release pharmaceutical compositions containing a polypeptide and a salt of an alginic acid. This invention also is directed to methods of treating inflammatory bowel diseases that are mediated by tumor necrosis factor, interleukin-6 or interleukin-1 by administering such controlled enteric release formulations to a patient.

BACKGROUND OF THE INVENTION

Inflammatory bowel disease (IBD) is marked by the presence of chronic inflammation of the gastrointestinal tract. One form of the disease is ulcerative colitis, a disease that affects the large bowel exclusively and which is characterized by mucosal ulceration, superficial inflammatory-cell infiltration of the bowel wall, and in extensive long-standing cases, neoplastic transformation. Another form of the disease is termed Crohn's disease (regional enteritis or regional ileitis). Crohir's disease can affect any part of the alimentary canal, from the mouth to the rectum, although it is commonly involved in the terminal ileum and the ascending colon. It has been recently reported that long-standing ulcerative colitis in patients is correlated to an increased incidence of colorectal cancer. See, for example, Lennard-Jones, et al., *Gut,* 31:800–806 (1986); and Ekbom et al., *N Engl. J. Med.,* 323:1228–1233 (1988). Furthermore, Crohn's disease has been firmly associated with an increased risk of colorectal cancer, Ekbom et al., *Lancet,* 336:357–359 (1990).

Approximately 10 percent of the cases involving either Crohn's disease or ulcerative colitis involve the same anatomic location, i.e., the large bowel. These two forms of inflammation are partly and possibly wholly distinct in their pathogenic events, however it also is likely that they share important common pathophysiologic processes. It was reported by odolsky, *N. Engl. J. Med.,* 325 (13): 928–937 (1991), that certain cytokines are mediators of the inflammation, namely, interlieukin-1 (IL- 1) and interleukin-6 (IL-6). Along with IL-1 and IL-6, Stevens, et al., *Dig. Dis. and Sciences,* 37 (6):818–826 (1992), recently reported that the pro inflammatory cytokine tumor necrosis factor-alpha (TNF-(α) was expressed in the intestine of patients with IBD.

The most commonly used management agents for IBD include corticosteroids and sulfasalazine. Sulfasalazine is a congener of sulfapyridine and 5-aminosalycylic acid. Podlosky, *N. Engl. J. Med.,* 325 (14): 1008–1016 (1991) reported that sulfasalazine acts, inter alia, as an inhibitor of prostaglandin synthase and 5-lipoxygenase. Sulfasalazine, while generally safe, is given to less than about 20 percent of the patients due to hypersensitivities such as rash, arthritis, pericarditis, pancreatitis and pleuritis. Corticosteroid use is somewhat limited by the considerable risk of side effects and potential complications. Additional drugs, such as clonidine, cromoglycate, chloroquine, interferon, and methotrexate are a few of the drugs described by Peppercorn as potential therapies for IBD in *Ann. Int. Med.* 112:50–60 (1990).

Another complication to effective treatment has been the delivery of medicament to the inflammatory site. The time during which an orally administered therapeutic material resides in the stomach is an important factor in terms of its absorption. Most drugs are optimally absorbed in the small intestine, and thus rapid gastric emptying can lead to early bioavailability of the drug. However, a prolonged bioavailability of the drug is possible through a delayed gastric emptying. Attempts have been made to prolong the residence time of drugs in transit through the gastrointestinal tract. A variety of slow-release formulations and controlled release formulations are well-known in the art, for example, hydroxypropyl methylcellulose phthalate, hydroxypropyl methylcellulose acetate succinate, and cellulose acetate phthalate.

A well known pH-sensitive material is alginate. Alginate is an anionic copolymer of 1,4-linked-β-D-mannuronic acid and α-L-guluronic acid. Various forms of alginate are available commercially. Such forms are typically 60% 1,4-linked-β-D-mannuronic acid and 40% α-L-guluronic acid; or 30% 1,4-linked-β-D-mannuronic acid and 70% α-L-guluronic acid. Alginic acid can spontaneously form a translucent gel when associated with calcium ions in an acidic environment. The use of alginate gel systems for sustained release drug delivery systems has been documented. The advantages of using an alginate gel delivery system for an orally-administered drug stems from the fact that alginate is non-toxic when taken orally, alginate beads can protect acid-sensitive drugs from gastric fluids, and provide the controlled release of drug when exposed to acidic environments. Examples of combinations of various drugs with alginate include Stockwell, et al., *J. Controlled Release,* 3:167–175 (1986) wherein sodium alginate delivery systems for the cationic drugs caffeine, sodium salicylate and chlorpheniramine are described. Segi, et al., *Chem. Pharm. Bull.,* 37:3092–3095 (1989) describe the cationic drug, propanolol, and its interaction with alginate gel beads. Another cationic drug, theophylline was examined with alginate gel beads by Bahkoo, et al., *Proc. Int. Symp. Controlled Release Bio. Mater.* 18:441–442 (1991).

The entrapment of proteinaceous materials has just recently been explored. The encapsulation of fibroblast growth factor-alpha (FGF), epidermal growth factor (EGF) transforming growth factor (TGF-α) in sodium alginate gel beads is described by Downs, et al., *J. Cell Physiol.,* 152:422–429 (1992). Downs et al. observed that the amount of protein entrapped within the alginate bead is dependent on the protein's electrostatic interactions with the alginate anion.

In view of the above, there remains the need in the art for an effective medicament for IBD and an efficient means of delivering such medicament to the site of inflammation.

SUMMARY OF THE INVENTION

The invention is directed to controlled release compositions for delivery of a polypeptide to the gastrointestinal region of a patient. Such controlled release formulations comprise an effective amount of a polypeptide selected from the group consisting of: (a) tumor necrosis factor (TNF) receptor, (b) interleukin- 1 receptor (IL- 1 R), (c) interleukin- 1 receptor antagonist (IL-1ra) and (d) a monoclonal antibody that is immunoreactive against TNF, IL-6 or IL- 1; and a salt of an alginic acid.

The invention also pertains to a method of treating gastrointestinal diseases mediated by IL-1, IL-6 or TNF, comprising administering to a patient in need thereof, a controlled enteric release pharmaceutical formulation comprising an effective amount of a polypeptide selected from the group consisting of: (a) TNF receptor, (b) interleukin-1 receptor (IL-1R), (c) interleukin-1 receptor antagonist (IL-1ra), (d) interleukin-6 receptor and (e) a monoclonal antibody that is immunoreactive against TNF, IL-6 or IL-1; and a salt of an alginic acid.

DETAILED DESCRIPTION OF THE INVENTION

The invention described herein is directed to pharmaceutical compositions that provide for the controlled release of an active ingredient in the gastrointestinal cavity of a patient. Such compositions provide for the delivery of polyleptide material to the lower intestine and comprise an effective amount of a polypeptide selected from the group consisting of: (a) tumor necrosis factor receptor (TNFR), (b) interleukin- 1 receptor (IL-1R), (c) interleukin-1 receptor antagonist (IL-1ra) and (d) a monoclonal antibody that is immunoreactive against TNF, IL-6 or IL- 1; and a salt of an alginic acid.

As used herein, "TNFR" refers to a genus of plasma membrane polypeptides, or fragments thereof, that bind independently with TNF. Two forms of TNFRs are known in the art and encompassed by this invention, a first TNFR is a 80 kD mature protein described by Smith, et al., *Science*, 248:1019–1022 (1990), incorporated herein by reference. A second TNFR is a 55–60 kD mature protein and is described in EP-A-0308,378; Schall, et al., Cell, 61:361–370 (1990); and Loeicscher, et al., *Cell*, 61:351–359 (1990), each of which is incorporated herein by reference. The term TNFR as used herein also contemplates the soluble portions or fragments of these two forms, which soluble portions predominantly include the extracellular domain of the proteins, maintain binding activity and which are capable of being secreted by a cell. Fusion proteins that include a TNFR are also contemplated by this invention. For example, dimeric fusions of two extracellular domains of the 80 kD TNFR with the constant domain of a human IgG 1 are well known (p80 TNFR:Fc) and is described by Mohler et al. , *J. Immun.*, 151(3):1548–1561 (1993), incorporated herein by reference. Similar fusions using the extracellular regions of the 55 kD TNFR with the constant domain of a human IgG 1 are included in this definition, and is described by Peppel, et al., *J. Exp. Med.*, 174:1483–1489 (1991), incorporated herein by reference.

The term "IL-1R" means a genus of plasma membrane polypeptides, or fragments thereof, that bind independently to IL-1. Two such IL-1Rs are known to exist, namely the Type I IL-1R and the Type II IL-1R. Such IL-1Rs and fragments thereof, are described in U.S. Pat. Nos. 5,319,071; 5,180,812; 5,081,228 and 4,968,607, and in each of which is incorporated herein by reference. Type II IL-1Rs are described in EP-A 0460846, incorporated by reference. The term IL- 1R as used herein also contemplates the soluble portions or fragments of these two forms, which soluble portions predominantly include the extracellular domain of the proteins, maintain binding activity and which are capable of being secreted by a cell.

The term "IL- 1ra" refers to a genus of polypeptides, and fragments thereof, that are capable of binding to the IL-1R to inhibit the binding of IL-1 thereto. An IL-1ra is described in Eisenberg, et al., *Nature*, 343:341–346 (1990), and incorporated herein by reference. The definition of IL-1ra includes the soluble fragments of IL-1ra, that predominantly contain the extracellular domain of the native protein, maintain binding activity and that are capable of being secreted.

The term "IL-6R" refers to a genus of polypeptides, and fragments thereof, that bind IL-6. Such fragments include the soluble portions of the IL-6R that predominantly include the extracellular domain of the native IL-6 protein, maintain binding activity and that are capable of being secreted. The IL-6R is described by Yamasaki, et al., *Science*, 241:825–828 (1988), Yamasaki et al., *J. Biochem.*, 108:673–676 (1990), incorporated herein by reference. Taga et al. *Cell*, 58:573–581 (1989) describe a neomycin-resistant T cell line that expresses a cDNA encoding human IL-6R.

Monoclonal antibodies against both IL-1α and IL-1β that are suitable for use in this invention are described by Luger et al., *Immunobiol.* 172:346–352 (1986), incorporated herein by reference. The antibodies described by Luger et al. are capable of inhibiting IL-1 activity. Monoclonal antibodies against TNFα and TNFβ that are suitable for use in this invention are described in U.S. Pat. No. 5,223,395 and International Patent WO 9216553, each of which is incorporated herein by reference.

The term "active ingredient" refers to the polypeptides described herein, i.e., TNFR, IL-1R, IL-1ra, IL-6R and a monoclonal antibody that is immunoreactive against TNF, IL-6 or IL-1; either singly or as mixtures.

The invention also pertains to a method of treating gastrointestinal diseases mediated by IL-1,IL-6 or TNF, comprising administering to a patient in need thereof, a controlled release pharmaceutical formulation comprising an effective amount of a polypeptide selected from the group consisting of: (a) TNFR, (b) IL-1R, (c) IL-1ra, (d) IL-6R and (e) a monoclonal antibody that is immunoreactive against TNF, IL-6 or IL-1; and a salt of an alginic acid.

In the compositions of the invention, the active ingredient is typically provided in amounts of about one (1) weight percent of the total composition, to about 75 weight percent of the total composition. Preferred ranges of active ingredient are from about 25 weight percent to about 50 weight percent. Typical alginate solutions used to prepare the beads can range from about 0.1 weight-to-volume percent to about 5 weight-to-volume percent. Preferred alginate solutions comprise about 0.5 weight-to-volume percent to about 2 weight-to-volume percent.

Since the inflammation in the gastrointestinal tract can occur at any point therein, it is desirable to utilize a delivery system that can easily be manipulated to deliver the active ingredient to the inflamed site. The release of an active ingredient at a certain stage of residence in the tract can be made by manipulating various parameters of the composition. The type of cation used to crosslink the alginate beads effects the release rate of the active ingredient, as does the type of polycation used to coat the bead surface, see FIGS. 1 and 2,and Example 1, below. Lyophilization of the active ingredient-alginate beads can lead to a significantly reduced release rate of active ingredient as compared to non-lyophilized beads. Example 2 and FIG. 3, below, illustrate the effect of such lyophilization. Another advantage of lyophilization of the beads is realized in that it can improve the shelf stability of the active ingredient. Further, by varying the amount of guluronic acid content in the alginate beads, release of the active ingredient can be effected either rapidly or slowly, see FIG. 4 and Example 3, below.

In addition to the above, the following examples are provided to illustrate the particular embodiments of the invention and are not to limit the scope thereof.

EXAMPLE 1
Preparation of TNFR:Fc—Alginate Complex

This example describes a procedure for preparing a TNFR:Fc—alginate hydrogel bead complex. Low viscosity alginate (LF 10/60) was obtained from Pronova Corp. A two percent (weight/volume) sodium-alginate solution was prepared in distilled water. The solution was stirred overnight and filtered through a 0.45 micron filtration unit. The two percent sodium-alginate solution was diluted 1:1 with 2 mg of TNFR:Fc. TNFR:Fc dimeric fusion protein was prepared according to the procedure described in Mohler, et al., *J. Immun.*, 151(3):1548–1561 (1993). Using a 3 ml plastic syringe with a 25⅜ gauge needle, the sodium-alginate solution that contained the protein was transferred dropwise (about 10 cm from the surface of the solution) into a 15 ml beaker containing 10 ml of a one percent crosslinking divalent cation solution ($Ca^{2+}$ as $CaCl_2$, $Ba^{2+}$ as $BaCl_2$ or $Sr^{2+}$ as $Sr(NO_3)_2$), with gentle stirring for 15 minutes. Approximately, 60 spherical beads of about 2 mm diameter were produced from one ml of alginate-protein solution. After 15 minutes, the beads were separated from the crosslinking solution by a 20 ml Bio-Rad disposable column. Unincorporated protein in the solution was determined spectrophotometrically at 280 nm. The beads that were retained in the column were washed with 20 ml distilled water. The washed beads were transferred to a 5 ml vial with 4 ml of 50 mM phosphate buffer (KPi), pH 7.4 (release/dissolution buffer) and incubated at 37° C. with gentle shaking at 100 RPM. The beads then were separated from solution using a Bio-Rad column as described above. Four ml of fresh KPi was added to the beads and the beads transferred to a new vial. The fresh KPi and transfer of beads was repeated every 30 minutes or 60 minutes. Protein release was also determined every 30 minutes or 60 minutes. The total time of release was four hours.

The results of the effect of the divalent cations on the release of TNFR:Fc from the beads is shown in Table I below.

TABLE I

Percent Cumulative Release of TNFR:Fc from Alginate Beads Crosslinked with Various Divalent Cations

| Time (hours) | $Ba^{2+}$ | $Sr^{2+}$ | $Ca^{2+}$ |
|---|---|---|---|
| 0 | 0 | 0 | 0 |
| 0.5 | 12 | 22 | 18 |
| 1.0 | 27 | 38 | 68 |
| 1.5 | 36 | 43 | 68 |
| 2.0 | 47 | 46 | 67 |
| 2.5 | 59 | 50 | 67 |
| 3.0 | 63 | 52 | 66 |
| 3.5 | 66 | 55 | 66 |
| 4.0 | 66 | 55 | 66 |

From Table I, the data show that both the Ba- and Sr-crosslinked beads displayed prolonged release profiles as compared to the Ca-crosslinked beads (3.5 hours versus 1 hour). The calcium-crosslinked beads were partially dissolved and formed clumps to such an extent at the 1 hour timepoint that accurate protein quantitation was difficult. The Ba-and Sr-crosslinked beads, however, retained a spherical shape throughout the study, and likely is due to a greater affinity of the $Ba^{2+}$ and $Sr^{2+}$ cations for the alginate anion than displayed by the $Ca^{2+}$ cation.

EXAMPLE 2
Effects of Poly-cation Coating on Release Kinetics of TNFR:Fc

To prepare a polycation coating on the beads, 0.1 percent poly-arginine (139 kDa), poly-histidine (19 kDa) or poly-L-lysine (44 kDa) was prepared in 2 mM Tris buffer, pH 7.4. After TNFR:Fc was incorporated into the beads using the procedure described above, the beads were incubated with 10 ml of the above polycation solution at room temperature for 30 minutes. The beads were rinsed in distilled water before suspension into the KPi release buffer. Protein release was determined every hour, and after four hours, the beads were hydrolyzed in 0.1 M HCl for one hour and then resuspended in KPi. After two hours in KPi, unincorporated protein in the solution was determined spectrophotometrically at 280 nm. The approximate percentage of release are shown in Table II below.

TABLE 11

Percent Cumulative Release of TNFR:Fc From Sr-Alginate Beads Coated with Various Polycations

| Time (hours) | Control | Poly-His | Poly-Arg | Poly-Lys |
|---|---|---|---|---|
| 0 | 0 | 0 | 0 | 0 |
| 1 | 10 | 0 | 11 | 18 |
| 2 | 18 | 0 | 12 | 18 |
| 3 | 23 | 0 | 12 | 18 |
| 4 | 26 | 0 | 12 | 18 |
| 6 | 65 | 35 | 69 | 52 |

The data in Table II demonstrate that polyhistidine was the most efficient cation among the three tested in its ability to retard release of TNFR:Fc from the beads. The polyhistidine coated beads released approximately no TNFR:FC until 4 hours, after which all beads were hydrolyzed in 0.1 M HCl for one hour, and then resuspended in KPi (pH 7.4).

EXAMPLE 3
Effects of Lyophilization on the Release Kinetics of TNFR:Fc in Alginate Beads Beads containing TNFR:Fc and alginate (70% guluronic acid content) were prepared as described above. The beads then were frozen at −70° C. for 2–4 hours. Lyophilization was carried out overnight with a Virtis Sentry 12SL lyophilizer. After lyophilization, the beads were immediately reconstituted in the KPi release/dissolution buffer. Table III shows the release kinetics of the lyophilized and non-lyophilized preparations in approximate percent cumulative release.

TABLE III

Percent Cumulative Release of TNFR:Fc From Lyophilized and Nonlyophilized Beads Containing 70% Guluronic Acid Content

| Time (hours) | Lyophilized | Non-Lyophilized |
|---|---|---|
| 0 | 0 | 0 |
| 0.5 | 10 | 15 |
| 1.0 | 15 | 30 |
| 1.5 | 18 | 33 |
| 2.0 | 22 | 36 |
| 3.0 | 24 | 43 |
| 4.0 | 27 | 50 |
| 20 | 70 | not available |

The data show that lyophilization of the beads results in more sustained release of TNFR:Fc than non-lyophilized beads. Only 27% of the protein was released in the first four hours as compared to 50% release of TNFR:Fc for nonlyophilized beads. In addition, 20 hours of time was required for the lyophilized beads to release 70% of the active ingredient.

EXAMPLE 4
Effect of Guluronic Acid Content on Release Kinetics of TNFR:Fc in Lyophilized Alginate Beads Two compositions of beads were prepared using different levels of guluronic acid in the alginate. The first composition contained an alginate having a 70% guluronic acid content and is commercially available. This composition is hereinafter referred to as alginate composition "A". The second composition comprised a 1:1 mixture of an alginate having a 40% guluronic acid content and an alginate having a 70% guluronic acid content. This resulted in a final mixture having a total guluronic acid content mathematically calculated to be 55%. This alginate mixture is hereinafter referred to as composition "B". In each case, the alginate had a concentration of about 1% by weight-to-volume in the final solution used to prepare the beads. The beads were lyophilized using the procedure described above. Release of TNFR:Fc was done in the 50 mM potassium phosphate buffer solution described above. Table IV shows how varying the guluronic acid content of the alginate used to prepare the beads can effect the release of the TNFR:Fc, cumulative release percentages are approximate.

TABLE IV

Percent Cumulative Release of TNFR:Fc From Lyophilized Beads of Different Guluronic Acid Content

| Time | Alginate Composition | |
|---|---|---|
| (hours) | A | B |
| 0 | 0 | 0 |
| 1 | 10 | 10 |
| 2 | 15 | 38 |
| 3 | 18 | 43 |
| 4 | 22 | 49 |
| 5 | 28 | 52 |
| 20 | 70 | 55 |
| 70 | — | 75 |

Alginate composition B caused a rapid release of TNFR:Fc within the first four hours as compared to alginate composition A. At a time point of approximately 15 hours, both compositions had released about the same cumulative percentage of active ingredient, i.e., 55%. However, after that point, alginate composition B produced a slower, but steady release of active ingredient as compared to the alginate composition A. Since the residence time of material in the human gastrointestinal tract can vary between several hours to 48 hours, the alginate composition can be optimized using a varied guluronic acid content for release of the active ingredient at a specific time, and thus to the specific site in the intestinal tract.

EXAMPLE 5
TNFR:Fc Release in Acid Environment

This example describes the release of TNFR:Fc from the above-described lyophilized TNFR:Fc-alginate beads when exposed to an acidic environment. Beads containing TNFR:Fc and alginate (70% guluronic acid content) were prepared as described above. The beads were lyophilized and placed in 0.1M HCl at pH 1.2 (simulated gastric juice) to determine if the protein would be released in the stomach. After 3 hours, the beads were washed with distilled water and suspended in the KPi buffer solution (pH 7.4) to simulate the environment of the small intestine. Table V below shows the data, percentage release is approximate.

TABLE V

Cumulative Percent Release of TNFR:Fc From Lyophilized Beads in 0.1 M HCl

| Time (hours) | Percent Released |
|---|---|
| 0 | 0 |
| 3 | 5 |
| 4 | 58 |
| 5 | 65 |

Table V shows that less than 10% of the TNFR:Fc was released into the pH 1.2 environment during the first 3 hours. Table V also shows that about 65% of the TNFR:Fc was released after 2 hours in the KPi buffer. A binding inhibition assay demonstrated that the TNFR:Fc was still biologically active after treatment with HCl. This data show that the active ingredient in the alginate beads is protected from an acid environment and is released in an active form as the pH is increased.

EXAMPLE 6
Release Kinetics of IL-1R From Alginate Beads

The IL-1R was prepared using published procedures. Alginate beads containing 70% guluronic acid and 2 mg of the Type I IL-1R were prepared following the same procedure used to make TNFR:Fc in Example 1, except that $Sr(NO_3)_2$ was used as the crosslinking cation. The release kinetics were determined in the same way as with TNFR:Fc. The amount of IL-1R released was determined at 280 nm every 30 minutes for a total of 90 minutes. The release kinetics of IL-1R are shown in Table VI below.

TABLE VI

Percent Cumulative Release of TNFR:Fc From Alginate Beads

| Time (hours) | Percent Released |
|---|---|
| 0 | 0 |
| 0.5 | 20 |
| 1.0 | 30 |
| 1.5 | 40 |

The data from Table VI show that 40% of the IL-1R active ingredient is released after 90 minutes in the pH 7.4 KPi environment. As expected, Table VI indicates that, like TNFR:Fc, the IL-1R release also can be controlled using alginate beads.

EXAMPLE 7
Preparation of Alginate Complexes for IL-1ra, IL-6R, Monoclonal Antibodies Against TNF, IL-1 or IL-6

Other active ingredients, i.e., IL-1ra, IL-6R, as well as monoclonal antibodies against TNF, IL-1 or IL-6, are prepared using methods described in the art. Alginate complexes for IL-1ra, IL-6R, as well as monoclonal antibodies against TNF, IL-1 or IL-6 are easily prepared by following the steps described in Example 1 above. A variety of release kinetic profiles can be made for each active ingredient by following the guidelines described above. Determination of the release kinetics for each protein are made using the procedures described in the examples above.

What is claimed is:
1. A controlled release pharmaceutical composition comprising TNFR in an amount effective to modulate the biological effects of TNF, wherein the TNFR is encapsulated in alginate and wherein

(a) the TNFR is p80 TNFR:Fc fusion protein present in an amount from about 1% to about 75% weight percent of the solid content, (b) the alginate contains from approximately 40% to approximately 70% guluronic acid, (c) the composition is coated with a polycation selected from the group consisting of poly-arginine, poly-histidine, and poly-lysine, and (d) the composition is lyophilized.

* * * * *